US007751872B2

(12) United States Patent
Clayman

(10) Patent No.: US 7,751,872 B2
(45) Date of Patent: Jul. 6, 2010

(54) PORTABLE ELECTROCARDIOGRAM

(76) Inventor: Henry M. Clayman, 5 Chippawa Cir., Santa Fe, NM (US) 87506

( * ) Notice: Subject to any disclaimer, the term of this patent is extended or adjusted under 35 U.S.C. 154(b) by 377 days.

(21) Appl. No.: 11/925,545

(22) Filed: Oct. 26, 2007

(65) Prior Publication Data
US 2009/0112105 A1    Apr. 30, 2009

(51) Int. Cl.
*A61B 5/0404*    (2006.01)
(52) U.S. Cl. .................. 600/509; 600/382; 600/393; 600/512
(58) Field of Classification Search ............ None
See application file for complete search history.

(56) References Cited

U.S. PATENT DOCUMENTS

| | | | |
|---|---|---|---|
| 4,535,783 A * | 8/1985 | Marangoni ................ | 600/524 |
| 5,184,620 A * | 2/1993 | Cudahy et al. ............ | 600/382 |
| 6,363,274 B1 * | 3/2002 | Scalisi et al. ............. | 600/523 |
| 7,300,406 B2 * | 11/2007 | Carter ...................... | 600/528 |
| 7,647,093 B2 * | 1/2010 | Bojovic et al. ............ | 600/509 |
| 2002/0019669 A1 * | 2/2002 | Berrang et al. ............ | 623/10 |
| 2002/0082491 A1 * | 6/2002 | Nissila ..................... | 600/391 |
| 2003/0028117 A1 * | 2/2003 | Hampton .................. | 600/509 |
| 2003/0045787 A1 * | 3/2003 | Schulze et al. ............ | 600/382 |
| 2003/0187363 A1 * | 10/2003 | Alroy ....................... | 600/509 |

* cited by examiner

*Primary Examiner*—Kennedy J Schaetzle
(74) *Attorney, Agent, or Firm*—Michael J. Buchenhorner

(57) ABSTRACT

An apparatus for measuring cardiac electrical activity of a patient includes: a malleable pad, a first electrocardiogram electrode, and a ground electrode. The pad includes: a right handle for grasping with the patient's right hand, the right handle including an electrocardiogram electrode; a left handle for grasping with the patient's left hand, the left handle also including an electrocardiogram electrode; and an electronic circuit configured for receiving electrical signals from the electrodes and also configured to invert the signals from the electrodes for transmission to a processor to produce a graphic recording of the differences in electrical potential between the electrodes. The pad also includes a multiplex cable for coupling the electronic circuit to leadwires attached to the electrocardiogram electrodes; and a port configured for coupling with the processor. The first electrode and the handle electrodes form an inverted Einthoven triangle with the first electrode at an apex of said triangle, being located anatomically superior to the horizontal axis formed by the second and third electrodes.

18 Claims, 8 Drawing Sheets

500

PORTABLE ELECTROCARDIOGRAM

CROSS-REFERENCE TO RELATED APPLICATIONS

None.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

Not Applicable.

FIELD OF THE INVENTION

The invention disclosed broadly relates to the field of equipment for monitoring the electrical activity of the heart, and particularly to portable electrocardiograph monitors.

BACKGROUND OF THE INVENTION

An electrocardiogram is a test that graphically records the electrical activity of the heart. The electrocardiogram or ECG (sometimes called EKG) is used worldwide as a relatively simple way of diagnosing many heart conditions. It records the small electric waves being generated during heart activity using body surface electrodes attached to a patient. The electrodes are placed in a particular pattern because electrical signals generated by a human heart appear in a characteristic pattern throughout the body, and on its surface A procedure developed by Willem Einthoven in 1901 interrelated three electrodes specifically oriented on the body (right arm, left arm, and left leg). These electrodes are at the apices of a physiological triangle known as Einthoven's triangle, as shown in FIG. 1a. The difference in electrical potential between the left and right arms is designated lead I; lead II is the difference in electrical potential between the left leg and right arm; and lead III is the difference in electrical potential between the left leg and left arm. Thus, the Einthoven triangle resembles a triangle standing on its tip "▼."

These electrodes provide bipolar recordings of the voltage differential between two electrodes. By convention, the positive electrode is placed on the left arm, with the negative electrode on the right arm. In the lead II configuration, the positive electrode is on the left leg and the negative electrode is on the right arm. Lead III has the positive electrode on the left leg and the negative electrode on the left arm. The limb leads can be attached to the end of the limb (wrists and ankles) or at the origin of the limb (shoulder or upper thigh). The difference in electrical potential between two of the electrodes constitutes the signal.

Referring to FIG. 1b there is shown a simplified illustration of a conventional electrocardiograph 100 in place on a patient. The ECG 100 requires at least three leads (therefore three electrodes are needed). These three electrodes are applied one on each of the patient's arms 110 and 112. The third electrode 120 is applied on the patient's left leg.

A fourth electrode 140 is placed on the patient's right leg as an electrical ground. The ground can be at other locations on the body but at a reasonable distance from the other electrodes to ensure a good signal. In addition, there are six precordial (chest) leads 160 designated $V_1$-$V_6$ (not shown here). Their conventional placement is illustrated in FIG. 1c.

The electrodes are easy to apply and this conventional placement of electrodes works well in a hospital setting and in doctor's office. The problem arises, however, when it is desirable and sometimes necessary for an ECG to be used outside of a conventional medical setting. For example, a patient with chronic heart problems may want to have a portable ECG in the home or the office. Airlines may find it necessary to have a portable ECG in airplanes for in-flight emergency use. The signals produced by a portable unit can be transmitted to a doctor on the ground who can then interpret the signals and advise the airline staff as to whether to use an on-board defibrillator.

Electrodes must be positioned in an anatomically correct pattern so that the readings are valid. One problem with this conventional electrode placement is that leg electrodes are not conducive to portability.

SUMMARY OF THE INVENTION

Briefly, according to an embodiment of the invention, an apparatus for measuring cardiac electrical activity of a patient includes: a malleable pad, a first electrocardiogram electrode, and a ground electrode. The pad includes: a right handle for grasping with the patient's right hand, the right handle including an electrocardiogram electrode; a left handle for grasping with the patient's left hand, the left handle also including an electrocardiogram electrode; and an electronic circuit configured for receiving electrical signals from the electrodes and also configured to invert the signals from the electrodes for transmission to a processor to produce a conventional graphic recording of the differences in electrical potential between the electrodes. The pad also includes a multiplex cable for coupling the electronic circuit to leadwires attached to the electrocardiogram electrodes; and a port configured for coupling with the processor. The first electrode and the handle electrodes form an inverted Einthoven triangle with the first electrode at an apex of said triangle, and anatomically superior to the horizontal axis formed by the second and third electrodes.

According to another embodiment of the present invention, a method for measuring cardiac electrical activity of a patient includes steps or acts of: forming an inverted Einthoven triangle of electrocardiograph electrodes on the patient, including steps of: attaching a first electrode to an ear of the patient; attaching an electrical ground electrode to the patient; attaching second and third electrocardiogram electrodes to locations on the patient to form a base of the inverted Einthoven triangle; wherein the electrodes are coupled to a connector by leadwires and wherein the connector is operatively coupled to a processor; and electronically inverting signals obtained from the electrodes to produce a conventional electrocardiogram recording using the processor.

BRIEF DESCRIPTION OF THE DRAWINGS

To describe the foregoing and other exemplary purposes, aspects, and advantages, we use the following detailed description of an exemplary embodiment of the invention with reference to the drawings, in which.

Figure 1A:
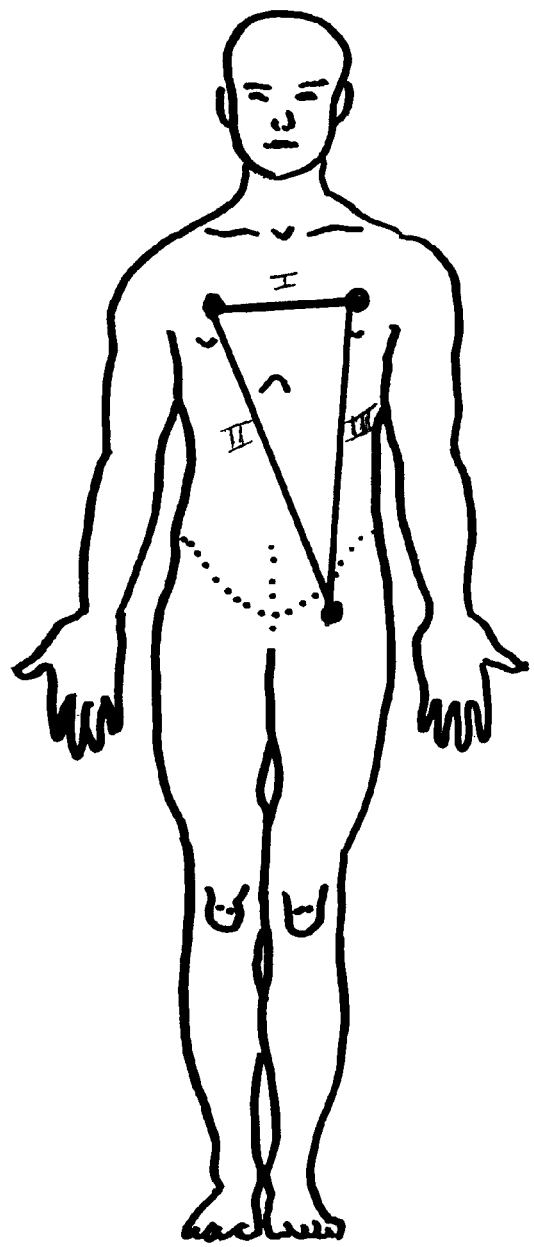
FIG. 1a shows an illustration of Einthoven's inverted triangle, according to the known art.
Figure 1B:
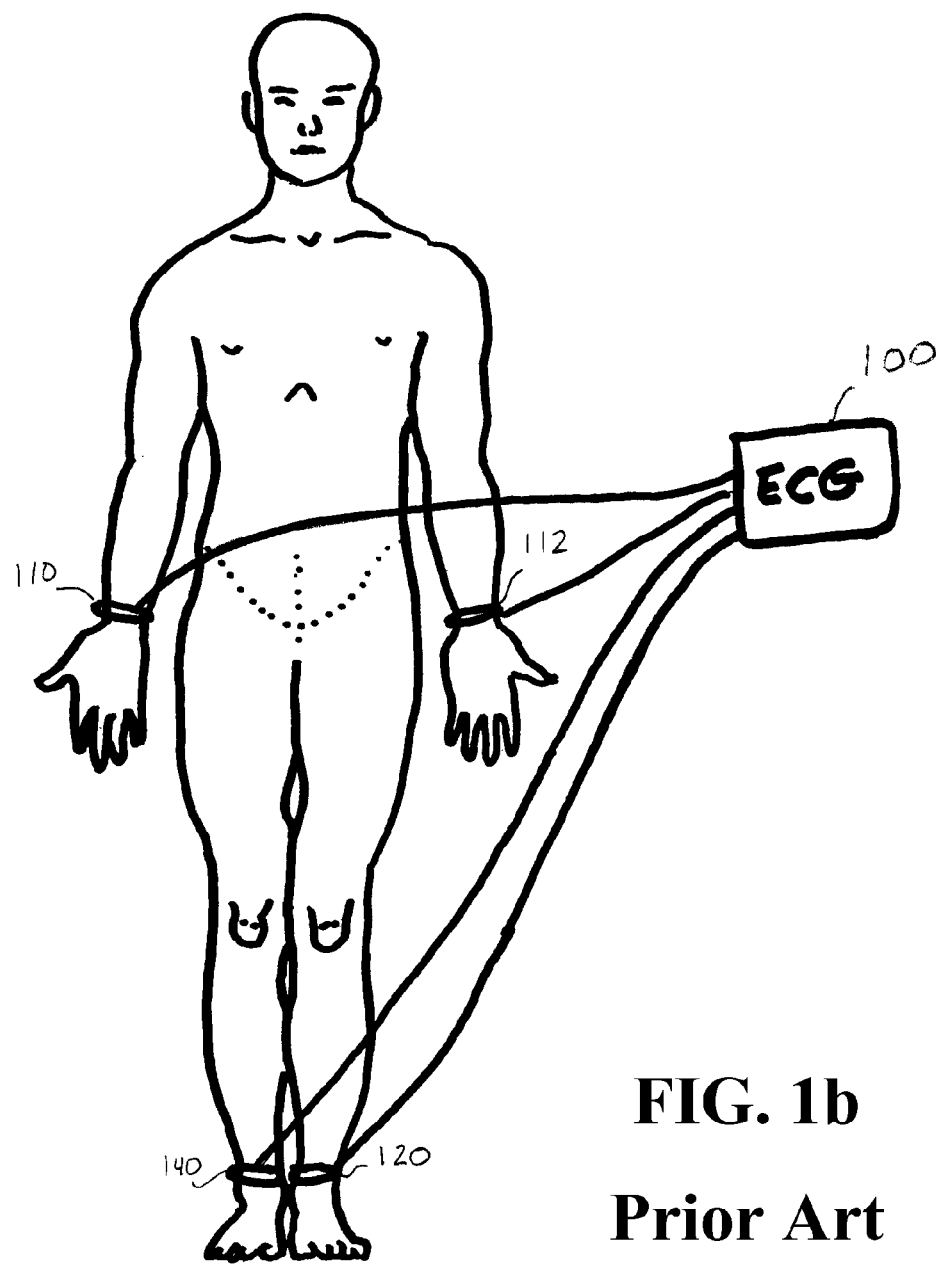
FIG. 1b shows an illustration of an electrocardiograph system according to the known art.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

I describe a method and apparatus for recording the electrical activity of the heart using an inverted Einthoven triangle of electrodes. The apparatus is a small, lightweight, and portable pad. The pad is expanded across a patient's chest in order to record electrical activity from the chest. It is constructed of a malleable material such as mylar, soft vinyl or rubber so that it can be easily contracted and expanded.

The pad forms the base of an inverted Einthoven triangle. The apex of the inverted Einthoven triangle is formed by a receiving electrode preferably located in or on the patient's ear. The other electrodes are preferably located on the pad which is placed across the patient's chest. This novel electrocardiograph system is small and portable so that it can be used for home use and travel. It embodies a small, compact form factor and can easily be carried in a small briefcase or travel bag. The portable system as will be described can be self-applied by a patient and is devoid of leg electrodes.

Figure 2:
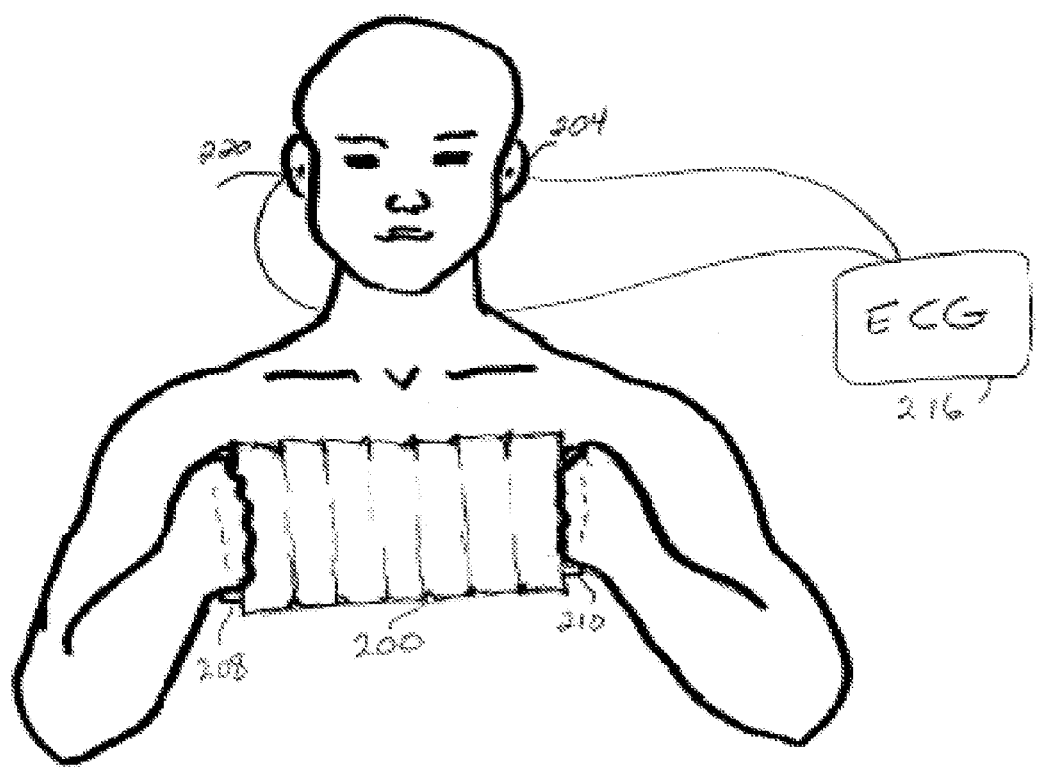
FIG. 2 shows an illustration of the portable electrocardiograph, according to an embodiment of the present invention.

Referring now in specific detail to the drawings, and particularly FIG. 2, there is illustrated a portable ECG device 200 according to an embodiment of the present invention. The device 200 is preferably a pad approximately the size of a book that expands to fit over a patient's chest. It contains electrodes for contact with a patient's chest, and hands.

Since patients have different size chests and their hearts may vary in location within the chest cavity, the pad 200 is adjustable to fit the different sizes and contours of almost all patients. The pad 200 expands and contracts like an accordion to adjust to the size and contour of a patient's chest. The pad 200 is constructed from any suitable material that will be pliable enough to bend and yet not interfere with electrical signals. A preferred embodiment uses accordion-like ribbed pleats, but other constructs are acceptable provided they are able to easily expand and contract.

The pad 200 includes two handles 208 and 210 at either end. In a preferred embodiment, each handle contains at least one receiving electrode for each respective hand. The patient grips both handles 208 and 210 to both position the pad 200 and provide electrical input from the arms. The patient holds the pad 200 lying substantially flat against the patient's chest.

The pad 200 preferably, but not necessarily, includes a number of electrodes embedded in the contact surface of the pad 200. As the pad 200 is held against the patient's chest, these electrodes make contact with the patient's skin and pick up intra-cutaneous electrical signals from the patient's heart.

One electrode 204 is placed in the patient's ear. Thus, electrical potential differences between the right arm, left arm, and ear can be measured. The ear electrode 204 forms the apex of the inverted Einthoven triangle, with the handles 208 and 210 forming the base of the triangle. Another electrode 220 used for ground potential may optionally be placed in the patient's contralateral ear as shown.

With electrode placement on the right arm, left arm, left ear and right ear (as ground), the combination of right arm-left arm is equivalent to a standard lead I ECG configuration. The right arm-left ear combination acts as an inverted lead II and the left arm-left ear combination acts as an inverted lead III. Readings from these two latter leads are transformed back to the conventional Einthoven configuration mathematically by taking into account: 1) the angular variation of the cardiac dipole measured by a left ear electrode as opposed to a left leg electrode; and 2) the magnitude variation of the cardiac dipole measured by a left ear electrode as opposed to a left leg electrode.

Figure 1C:
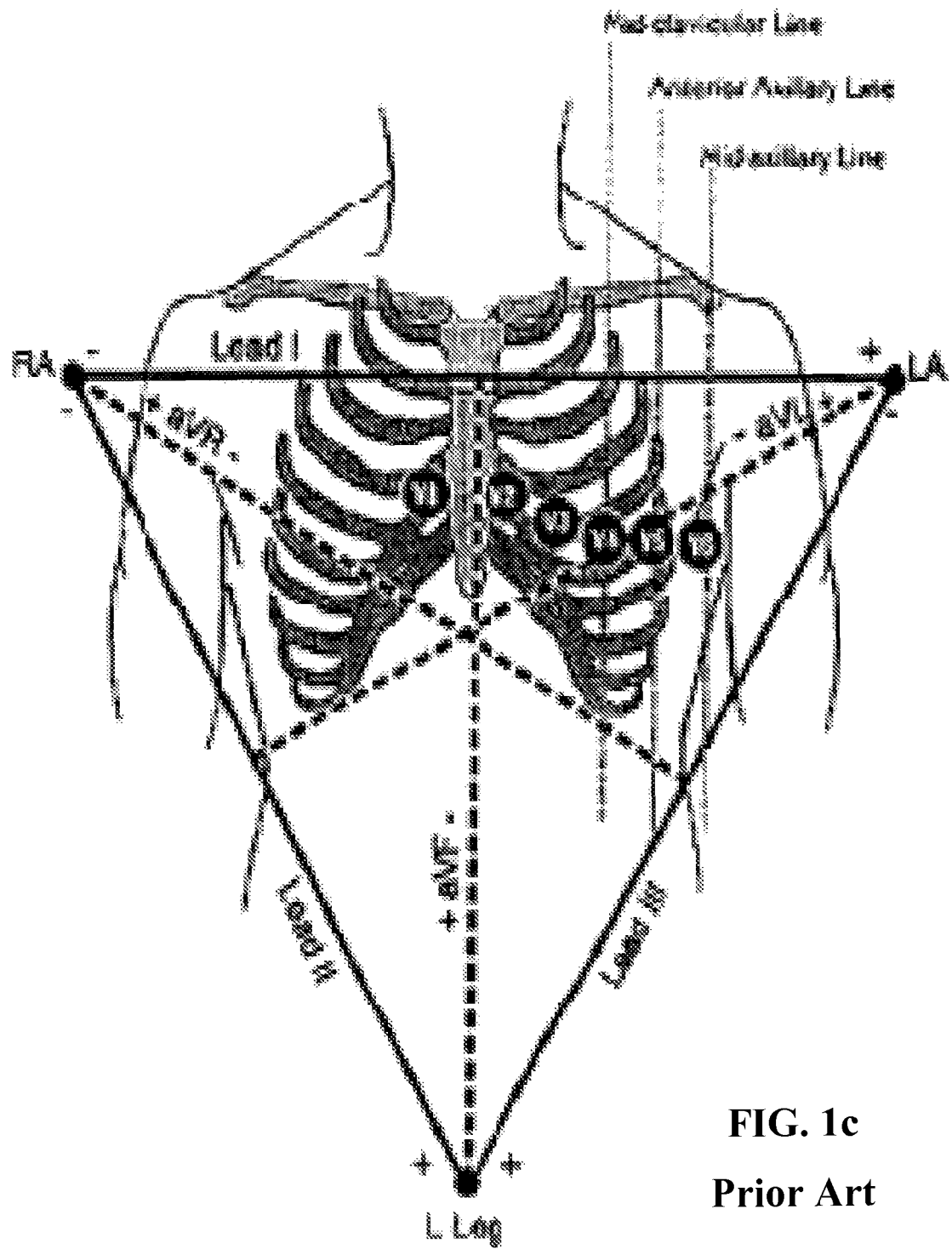
FIG. 1c shows the placement of leads $V_1$-$V_6$, according to the known art.
Figure 3A:
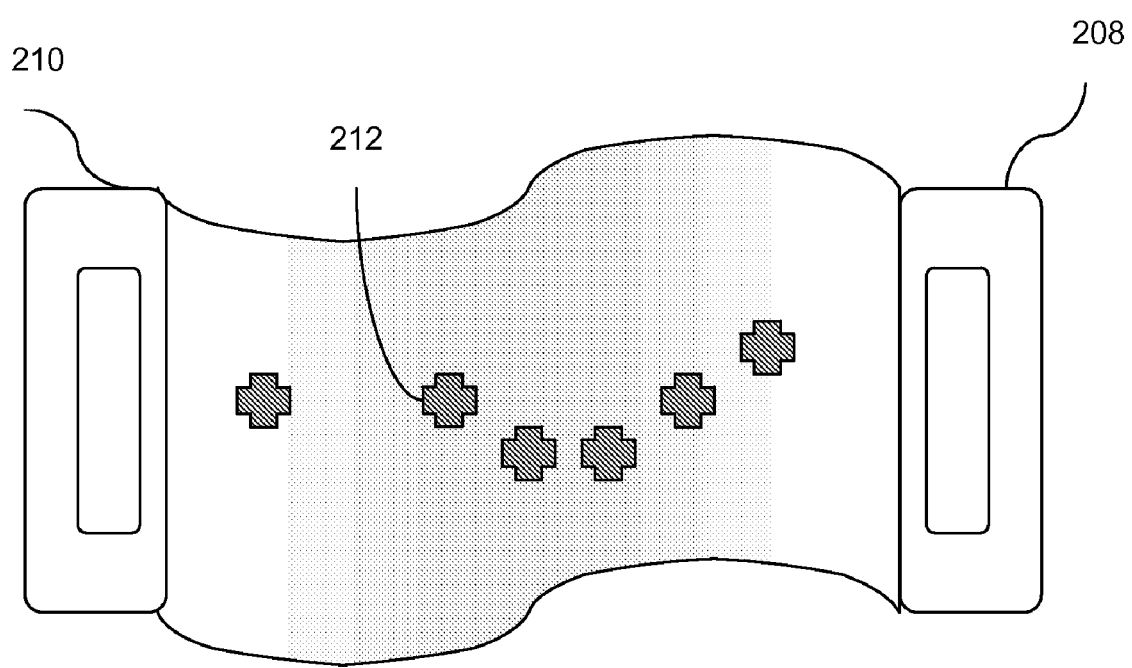
FIG. 3a shows the malleable form factor of the portable electrocardiograph, according to an embodiment of the present invention.

Referring to FIG. 3a, a closer view of the device 200 is shown, from the contact side that lies against a patient's chest. This embodiment carries six additional electrodes 212. The placement of these six additional electrodes 212 substantially correlates to the $V_1$-$V_6$ voltages as shown in FIG. 1c.

Figure 3B:
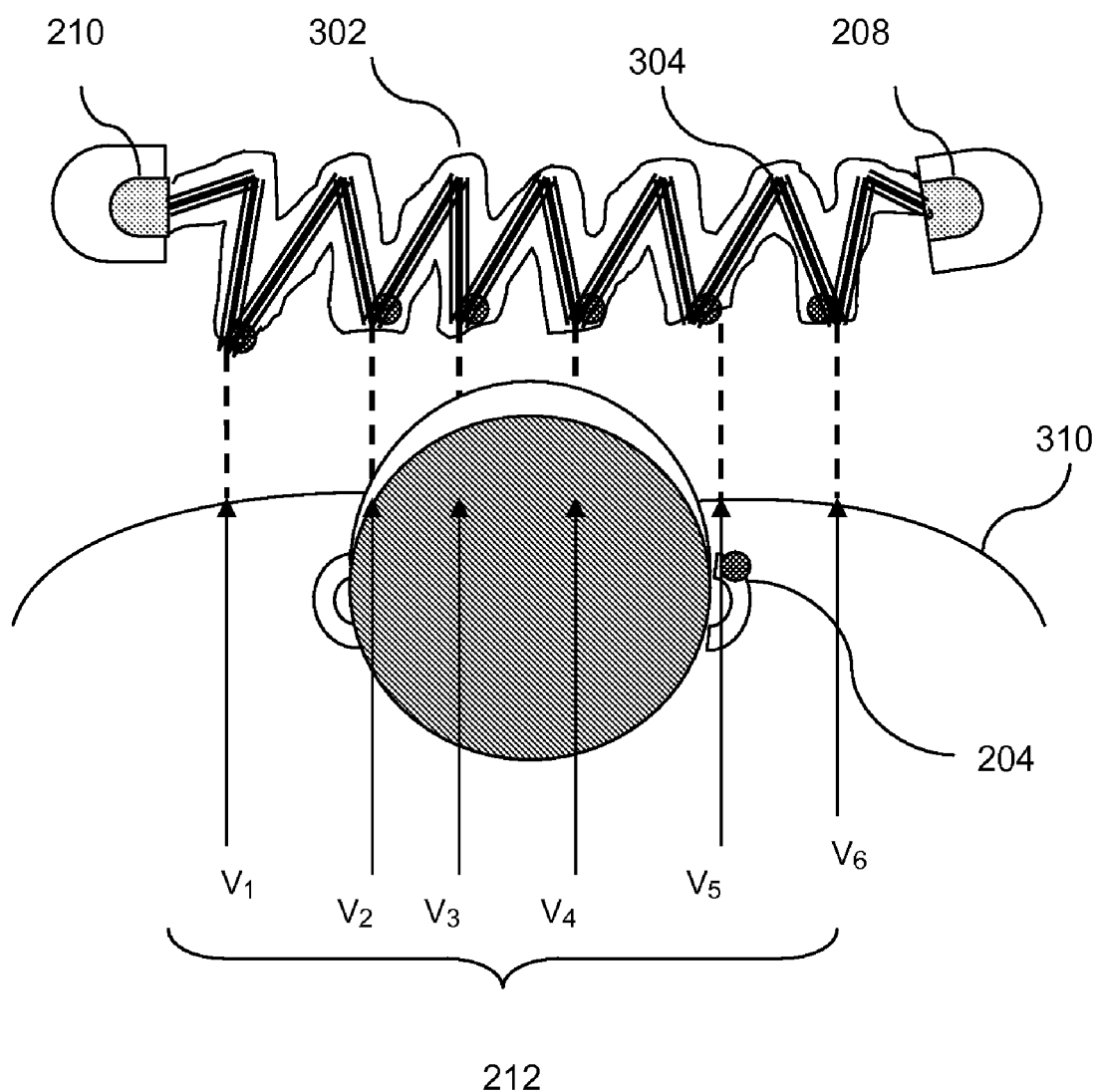
FIG. 3b shows, in sagittal view, the electrodes at the apices of each hinged articulation, according to an embodiment of the present invention.

Referring to FIG. 3b, the pad 200 is shown from a side view as seen from behind the patient, as it is expanded and ready to be placed over a patient's chest 310. The patient is holding the handles 208 and 210 and has expanded the pad 200 to comfortably fit on the patient's chest 310. Electrodes 212 are located on the contact surface of the pad 200 so that the voltages $V_1$-$V_6$ can be measured. The dashed lines indicate where the electrodes 212 will make contact with the patient's chest 310. The patient grasps the handles 208 and 210, and expands the pad 200 across his/her chest 310 while lying down flat. The patient, or an assistant, then positions the pad 200 by pressing down against the skin surface so that the electrodes 212 are in good contact with the surface of the chest 310. The pad 200 not only houses the electrodes and leadwires, it also acts as an electrical insulator between the electrodes and the patient, and between adjacent electrodes.

The embodiment of FIG. 3b uses an accordion principle to accommodate the size and contour of an individual patient's chest 310. The pad 200 has been expanded such that enclosed "pleats" 304 form oblique angles with electrodes 212 $V_1$-$V_6$ at the apex of each "pleat" 304. The pleats 304 provide support and are formed from a stiff, yet bending material. They produce the effect as seen in the ribs of an umbrella. The pleats 304 are encased in a compliant, non-conductive material 302 such as rubber, mylar, silicone, or any other appropriate material. The pleats 304 may be hinged. The electrodes 212 are disposed on the contact surface of the non-conductive material so that they can make contact with the patient's chest 310. Additional electrodes may also be placed in the pad 200. For example, a twelve lead system may be configured by the addition of six more electrodes 212. The handles 208 and 210 also contain electrodes 212 to be used in place of the conventional arm electrodes, with contact effected by the grasping actions of the hands.

Figure 4A:
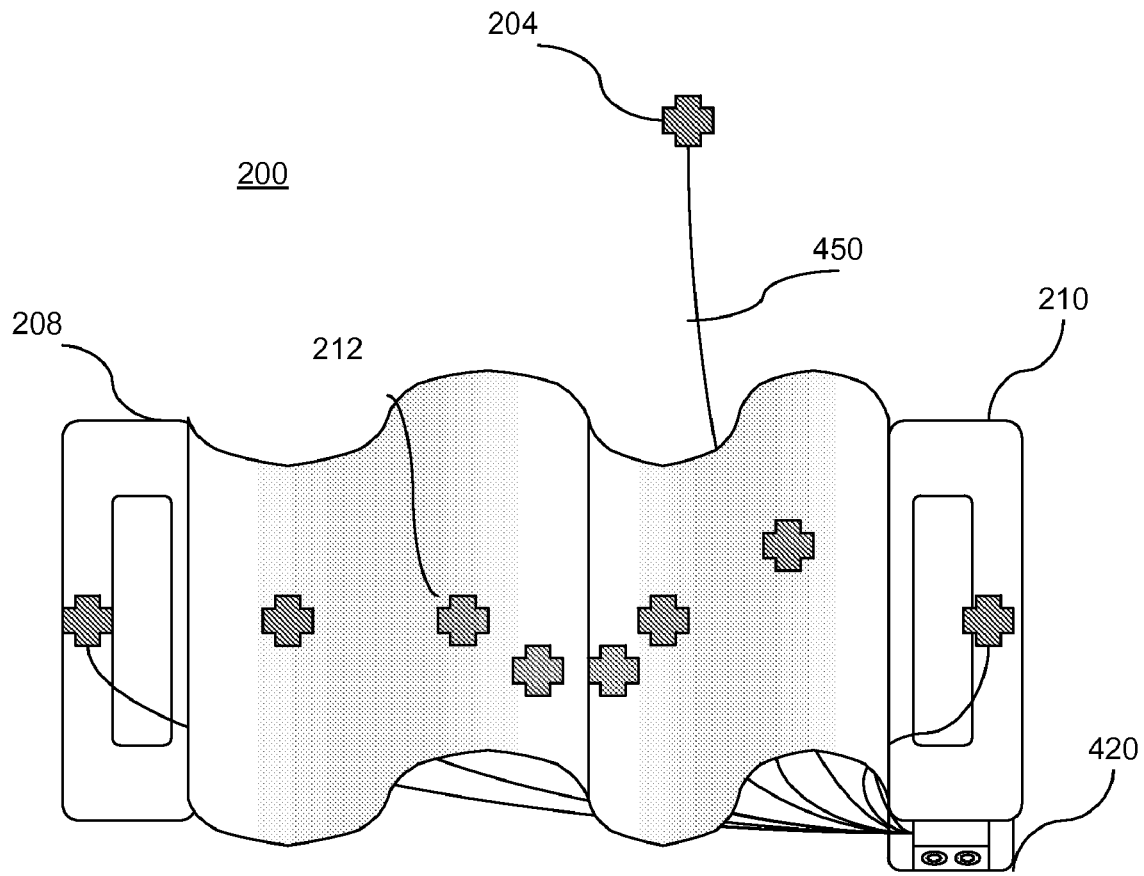
FIG. 4a shows the contact side of the pad placed against the patient's chest, illustrating the exposed electrodes, according to an embodiment of the present invention.

FIG. 4a shows the contact surface of the pad 200 which is placed against the patient's chest. The wires 450 extend from the electrodes 212 through the pad 200 to an electronic circuit 460 housed within a connector 420. The wires 450 may be combined into a multiplex cable (not shown). The electronic circuit 460, as used in conventional ECG devices, additionally inverts the electrical signals received from the electrodes to produce a conventional cardiac signal, which can be displayed on a monitor or transmitted to a remote location by landline or wireless adapter means.

Figure 4B:
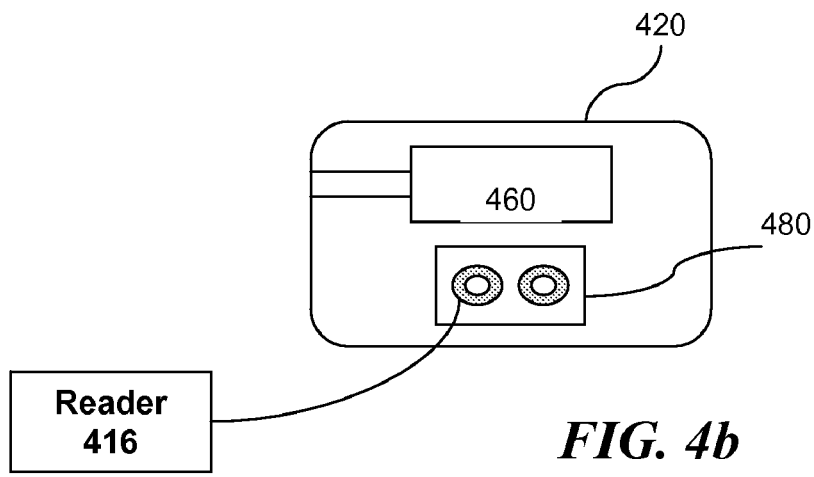
FIG. 4b shows a closer view of the connector, according to an embodiment of the present invention.

FIG. 4*b* shows a close-up view of an exemplary connector 420. One end of the connector 420 may be exposed outside of the pad 200. A port 480 is located at this end for allowing the pad 200 to be coupled with the reader 416. The reader 416 is used to read the electrical signals transmitted from the electrodes 200. The reader 416 comprises a processor, an amplifier, and a filter. It is preferably operatively coupled with a monitor or printer. The reader 416 may be a conventional ECG monitor. The electronic circuit 460 may be placed as shown within the connector 420, or the circuit 460 may be placed in any configuration that provides access to the wires 450.

Figure 5:
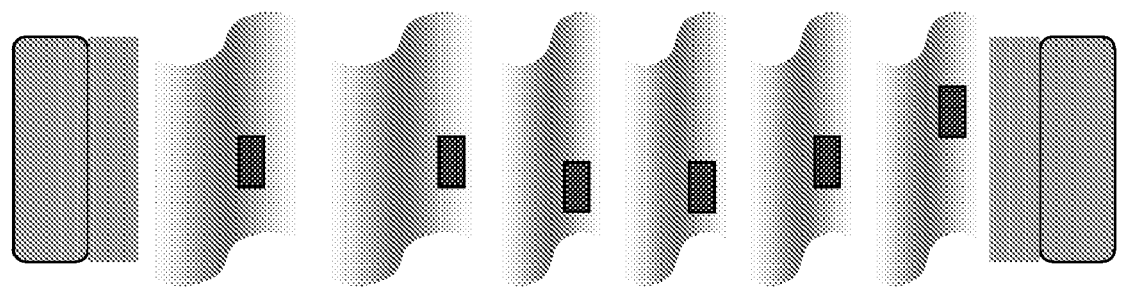
FIG. 5 shows the ECG pad with serpentine folds and $V_1$-$V_6$ electrodes, according to an embodiment of the present invention.

FIG. 5 shows another embodiment using a pad 500 with serpentine folds to achieve the accordion effect. In this embodiment the accordion effect may be achieved using bendable ribs inserted into the pad 200.

To complete the inverted Einthoven triangle, a receiving electrode 204 is attached to the patient's ear. This electrode 204 may be in an earphone form factor, or it may be clipped to the earlobe. Another electrode can be placed in the patient's contralateral ear and act as an electrical ground 220. Six electrodes 212 can be placed on the pad 200 to measure the $V_1$-$V_6$ voltages for added reliability. Additional electrodes may be placed in the handles 208 and 210.

The electrodes 212 can be rectangular or some other shape. They may be suction, button, or plate electrodes. Alternatively, the electrodes 212 may be printed on the pad 200. Each electrode has a substantially flat surface for secure attachment to a patient's skin. Modern electrodes are self-adhesive; but to aid in electrical conduction, a conductive gel can be applied to the flat surface of each electrode 212 before attachment. If necessary, tape can be used to secure the electrode 212. The non-contact surface of the electrode 212 is a conductor attached to an electrode leadwire 450 which in turn may be attached to a multiplex cable secured within the pad 200. The cable is coupled with the connector 420. The connector 420 includes ports for coupling with the reader 416 and other input/output devices.

To facilitate use by non-medical personnel, standardized color coding of the electrodes and/or leadwires can be used, and the color codes should be made available to the patient. For example, the non-contact surface of the pad 200 may have the color codes printed on it. The non-contact surface of the pad 200 may optionally be marked with indicators showing optimal placement in order to assure that the maximum number of signals are received.

In one embodiment, the minimum number of electrodes that can be advantageously used for cardiac monitoring is four: one receiving electrode in the patient's ear, two electrodes on the pad handles, and one electrode to be used as ground. This ground electrode may be placed in the patient's contralateral ear. In another embodiment, additional electrodes can be embedded or affixed to the pad 200, as has been previously shown.

Therefore, while there has been described what is presently considered to be the preferred embodiment, it will be understood by those skilled in the art that other modifications can be made within the spirit of the invention.

The invention claimed is:

1. A method for measuring cardiac electrical activity of a patient, the method comprising steps of:
    superimposing an inverted Einthoven triangle of electrocardiograph electrodes on the patient, the step of superimposing comprising steps of:
        attaching a first electrode to an ear of the patient, the first electrode forming an apex of the superimposed inverted Einthoven triangle;
        attaching an electrical ground electrode to the patient;
        attaching second and third electrodes to locations on the patient to form a base of the inverted Einthoven triangle;
    wherein the electrodes are coupled to a connector by leadwires and wherein the connector is operatively coupled to a processor; and
    electronically inverting signals obtained from the electrodes to produce a conventional electrocardiogram recording using the processor.

2. The method of claim 1, further comprising attaching the electrical ground electrode to the patient's contralateral ear.

3. The method of claim 2, wherein the first electrode attached to the ear is an earphone.

4. The method of claim 1 wherein the second electrode is attached to the patient's right arm such that a pairing of the right arm and the ear act as an inverted lead II; and wherein the third electrode is attached to the patient's left arm such that a pairing of the left arm and the ear act as an inverted lead III; and wherein a pairing of the right arm and the left arm act as lead I.

5. The method of claim 4 wherein electronically inverting signals further comprises:
    mathematically transforming readings taken from leads II and III back to a conventional Einthoven configuration by taking into account: an angular variation of a cardiac dipole measured by the ear electrode as opposed to a left leg electrode; and a magnitude variation of the cardiac dipole measured by the ear electrode as opposed to a left leg electrode.

6. The method of claim 1, further comprising:
    placing a malleable pad comprising handles and the connector over the patient's chest; and
    deforming the malleable pad to adjust it to the patient's chest.

7. The method of claim 6 wherein handles comprise the second and third electrodes and wherein the patient grasps each handle with a hand.

8. The method of claim 7 further comprising: placing six additional electrodes on the malleable pad, the six electrodes representing cardiac leads v1 through v6.

9. An apparatus for measuring cardiac electrical activity of a patient, the apparatus comprising:
    a malleable pad comprising a conformable non-conductive material for placing over the patient's chest, the malleable pad comprising:
        a right handle for grasping with the patient's right hand, said right handle comprising an electrocardiogram electrode;
        a left handle for grasping with the patient's left hand, said left handle comprising an electrocardiogram electrode;
        an electronic circuit configured for receiving electrical signals from the electrocardiogram electrodes and also configured to invert the signals from the electrocardiogram electrodes for transmission to a processor to produce a conventional graphic recording of the differences in electrical potential between the electrodes; and a port configured for coupling with the processor; and a first electrode, one surface of said first electrode being configured for attachment to the patient's ear and the other surface of said first electrode configured to conduct electrical voltage to the electronic circuit; and a ground electrode for coupling to ground potential;

wherein the first electrode and the handle electrodes form an inverted Einthoven triangle with the first electrode comprising an apex of said triangle.

10. The apparatus of claim 9 wherein the malleable pad comprises pleats allowing the malleable case to expand and contract to conform to the patient's chest.

11. The apparatus of claim 10 wherein each of the apices of the pleats are in contact with the patient's chest and wherein the pleats comprise electrocardiogram electrodes corresponding to $V_1$-$V_6$ voltages and wherein the electrocardiogram electrodes are disposed on a contact surface of the apparatus.

12. The apparatus of claim 10 wherein the pleats are hinged.

13. The apparatus of claim 9 wherein the malleable pad comprises serpentine folds.

14. The apparatus of claim 9 wherein the ground electrode is configured for attachment to the patient's contralateral ear for coupling to ground potential.

15. The apparatus of claim 9 further comprising the processor and wherein the malleable pad further comprises a wireless adapter configured for wireless transmission to the processor.

16. The apparatus of claim 15 wherein the processor is an electrocardiograph device.

17. The apparatus of claim 9 further comprising leadwires wherein one leadwire is coupled with each electrocardiogram electrode.

18. The apparatus of claim 17 further comprising a multiplex cable for coupling the leadwires to the electronic circuit.

* * * * *

UNITED STATES PATENT AND TRADEMARK OFFICE
CERTIFICATE OF CORRECTION

PATENT NO. : 7,751,872 B2  Page 1 of 1
APPLICATION NO. : 11/925545
DATED : July 6, 2010
INVENTOR(S) : Henry M. Clayman It is certified that error appears in the above-identified patent and that said Letters Patent is hereby corrected as shown below:

Title page, Item (75) Inventor

Please change the inventor's city/state on the patent to read:
Miami, FL

The inventor's address has changed to:

12555 Biscayne Blvd.
PMB709
Miami, Florida 33181

Signed and Sealed this

Seventh Day of December, 2010

David J. Kappos
*Director of the United States Patent and Trademark Office*